(12) United States Patent
Ueoka et al.

(10) Patent No.: US 6,875,895 B2
(45) Date of Patent: Apr. 5, 2005

(54) BIS (DIPHENYLVINYL) ARENE COMPOUND

(75) Inventors: Takahiro Ueoka, Tsukuba (JP); Hideyuki Ikehira, Mukou (JP); Yoshiaki Tsubata, Tsukuba (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/223,211

(22) Filed: Aug. 20, 2002

(65) Prior Publication Data

US 2003/0100786 A1 May 29, 2003

(30) Foreign Application Priority Data

Aug. 31, 2001 (JP) ........................ 2001-263146

(51) Int. Cl.[7] ................ C07C 25/28; C07C 43/225; C07F 7/08
(52) U.S. Cl. ............ 568/633; 556/489; 558/58; 558/413; 558/423; 558/428; 558/489; 560/10; 560/11; 560/100; 560/101; 560/139; 560/140; 560/640; 560/641; 560/928; 560/929; 568/58; 568/641; 570/128; 570/183; 570/184
(58) Field of Search ............ 558/58, 413, 423, 558/428, 489; 560/10, 11, 100, 101, 139, 140, 640, 641, 928, 929; 568/58, 633, 641; 570/128, 183, 184; 556/489

(56) References Cited

U.S. PATENT DOCUMENTS

| 4,076,645 | A | | 2/1978 | Vega | |
|---|---|---|---|---|---|
| 5,486,441 | A | | 1/1996 | Matsushima et al. | |
| 5,503,910 | A | * | 4/1996 | Matsuura et al. | 428/212 |
| 6,337,150 | B1 | * | 1/2002 | Kwon et al. | 428/690 |
| 6,337,160 | B1 | | 1/2002 | Kwon et al. | |
| 6,444,334 | B1 | * | 9/2002 | Doi et al. | 428/690 |

FOREIGN PATENT DOCUMENTS

| EP | 0 502 202 A1 | 9/1992 |
|---|---|---|
| JP | 5-230202 A | 9/1993 |
| JP | 2000-143778 A | 5/2000 |

OTHER PUBLICATIONS

J. Malinsky et al., "Molecular Self–Assembly Approaches to Multilayer Organic Light–Emitting Diode Structures", Proc. SPIE–Int. Soc. Opt. Eng., vol. 3281, (1998), pp. 148–155 with Abstract.

* cited by examiner

Primary Examiner—Peter O'Sullivan
(74) Attorney, Agent, or Firm—Sughrue Mion, PLLC

(57) ABSTRACT

Provided is a bis(diphenylvinyl)arene compound having a reactive functional group on phenyl group, represented by below formula (1),

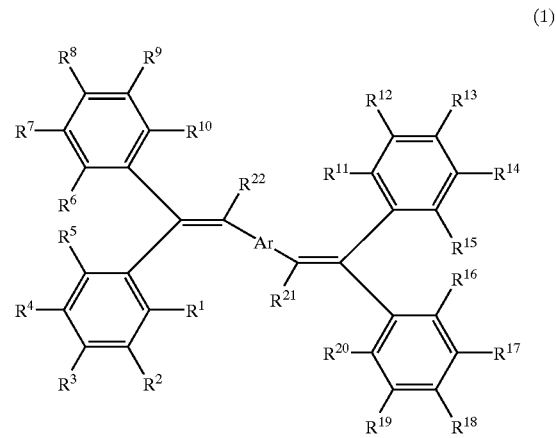

(1)

wherein, Ar is an arylene group and has one or more substituents; $R^1$–$R^{22}$ each independently represent a hydrogen atom, a halogen atom, cyano group, nitro group, etc., and at least one of $R^1$–$R^{20}$ is a halogen atom, etc. The arene compound has sufficient solubility in an organic solvent and excellent reactivity.

5 Claims, No Drawings

BIS (DIPHENYLVINYL) ARENE COMPOUND

BACKGROUND OF THE INVENTION

1. Field of the Invention

The present invention relates to a bis(diphenylvinyl)arene compound.

2. Description of the Related Art

As a bis(diphenylvinyl)arene compound having a reactive functional group such as a halogen atom, for example, JP-A-2000-143778 discloses bis(diphenylvinyl)benzene having two bromine atoms on phenyl group, and a polymer obtained by polymerizing this compound can be used as a light-emitting material.

However, the above bis(diphenylvinyl)arene compound having a reactive functional group is not sufficiently soluble in an organic solvent, therefore the reactivity such as polymerization is also still insufficient.

An object of the present invention is to provide a new bis(diphenylvinyl)arene compound having a reactive functional group on the phenyl group, which has sufficient solubility in an organic solvent and excellent reactivity.

The present invention relates to a bis(diphenylvinyl)arene compound shown by formula (1),

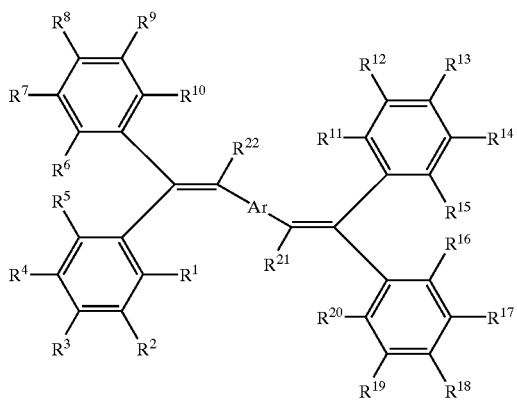

(1)

wherein, Ar is an arylene group and has one or more substituents selected from alkylsilyl group, alkoxy phenyl group, arylsulfonyloxy group, alkylsulfonyloxy group, alkyl group, alkenyl group, aralkyl group, arylthio group, aryl alkenyl group, cyclic alkenyl group, alkoxy group, aryloxy group, alkyloxy carbonyl group, aralkyloxy carbonyl group, aryloxy carbonyl group, and aryl group; $R^1$–$R^{22}$ each independently represent a hydrogen atom, a halogen atom, cyano group, nitro group, arylsulfonyloxy group, alkylsulfonyloxy group, alkyl group, alkenyl group, aralkyl group, arylthio group, arylalkenyl group, cyclic alkenyl group, alkoxy group, aryloxy group, alkyloxy carbonyl group, aralkyloxy carbonyl group, aryloxy carbonyl group, or aryl group; and at least one of $R^1$–$R^{20}$ is a halogen atom, arylsulfonyloxy group or alkyl sulfonyloxy group.

The arylene group is an atomic group in which two hydrogen atoms are removed from an aromatic hydrocarbon. The aromatic hydrocarbon here also includes those having a condensed ring, and those in which two of independent benzene rings or condensed rings are bonded through a direct bond or vinylene group. The arylene group usually has about 6 to 20 carbon atoms. Here, the number of carbon atoms of an arylene group does not contain the carbon atoms of the substituent. As the arylene group, specifically exemplified are phenylene group, naphthalenediyl group, and anthracene diyl group, etc. In view of availability of the raw material and reactivity, phenylene group is preferable.

Next, the substituent contained in the arylene group is explained.

Examples of the substituents include: triethylsilyl group, tripropylsilyl group, tributylsilyl group, dimethyloctylsilyl group, etc., as alkylsilyl group; methoxyphenyl group, ethoxyphenyl group, propoxyphenyl group, 3,7-dimethyloctyloxy phenyl group etc., as alkoxyphenyl group; p-toluene sulfonyloxy group, phenyl sulfonyloxy group etc., as arylsulfonyloxy group; propylsulfonyloxy group, trifluoromethyl sulfonyloxy group etc., as alkyl sulfonyloxy group; methyl group, ethyl group, n-propyl group, isopropyl group, n-butyl group, isobutyl group, t-butyl group, n-amyl group, neopentyl group, n-hexyl group, cyclohexyl group, n-octyl group, n-nonyl group, 2,3,4-trimethyl-3-pentyl group, 2,4-dimethyl-3-pentyl group etc., as alkyl group; benzyl group, 2-phenylethyl group, 2-naphtylethyl group, diphenylmethyl group, etc., as aralkyl group; phenyl group, naphtyl group, biphenyl group, furyl group, etc., as aryl group; thiophenyl group etc., as arylthio group; 2-methyl-1-propenyl group, 2-butenyl group etc., as alkenyl group; trans-β-styryl group, 3-phenyl-1-propenyl group etc., as aryl alkenyl group; 1-cyclohexenyl group etc., as cyclic alkenyl group: methoxy group, ethoxy group, n-propoxy group, t-butoxy group etc., as alkoxy group; phenoxy group, naphtyloxy group, diphenyloxy group etc., as aryloxy group; methoxy carbonyl group, ethoxy carbonyl group, t-butyloxy carbonyl group, as alkyloxy carbonyl group; and benzyloxy carbonyl group etc., as aralkyloxy carbonyl group; and phenyloxy carbonyl group etc., as aryloxy carbonyl group, respectively. Moreover, the above substituents may be substituted by, for example: halogen atoms such as fluorine atom, chlorine atom, bromine atom, iodine atom; alkoxy groups such as methoxy group, ethoxy group, n-propoxy group, t-butoxy group, etc.; aryloxy groups such as phenoxy group, etc.; lower alkyl groups such as methyl group, ethyl group, n-propyl group, isopropyl group, n-butyl group, isobutyl group, t-butyl group, n-amyl group, neo pentyl group, n-hexyl group, etc.; lower alkylthio groups such as n-propylthio group, t-butylthio group, etc.; arylthio groups such as phenylthio group, etc.; nitro group; hydroxyl group, etc.

Further, these substituents may form a ring and may have a saturated or unsaturated condensed-ring structure.

Among them, alkyl group, alkylsilyl group, and alkoxy phenyl group are preferable in view of solubility. The number of these substituents is one or more, and usually 1 to 4.

Next, $R^1$–$R^{22}$ of formula (1) are explained.

In formula (1), $R^1$–$R^{22}$ may be the same or different from each other, and represent a hydrogen atom, a halogen atom, cyano group, nitro group, arylsulfonyloxy group, alkylsulfonyloxy group, alkyl group, alkenyl group, aralkyl group, arylthio group, arylalkenyl group, cyclic alkenyl group, alkoxy group, aryloxy group, alkyloxy carbonyl group, aralkyloxy carbonyl group, aryloxy carbonyl group, or aryl group. Here, at least one of $R^1$–$R^{20}$ is a halogen atom, an aryl sulfonyloxy group, or an alkylsulfonyloxy group.

A halogen atom, aryl sulfonyloxy group, or alkyl sulfonyloxy group may be available as a reactive group, such as for polymerization. What is necessary is just to have one group of these, but in order to be used as a monomer for polymerization, preferable is to have two or more groups of these.

When the number of halogen atom, arylsulfonyloxy group, or alkylsulfonyloxy groups is one, it is preferable that $R^3$ in formula (1) is a halogen atom, arylsulfonyloxy group, or alkyl sulfonyloxy group.

Moreover, when the number is two, it is preferable that $R^3$ and $R^{13}$ are halogen atoms, arylsulfonyloxy groups, or alkylsulfonyloxy groups.

In $R^1$–$R^{22}$ of formula (1), fluorine atom, chlorine atom, bromine atom, and iodine atom, etc. are exemplified as the halogen atom, and chlorine atom and bromine atom are preferable.

As the arylsulfonyloxy groups, exemplified are p-toluene sulfonyloxy group, phenyl sulfonyloxy group, etc.; and as the alkylsulfonyloxy groups, exemplified are propylsulfonyloxy group, trifluoromethyl sulfonyloxy group, etc. Among them, p-toluene sulfonyloxy group and trifluoro methyl sulfonyloxy group are preferable in view of ready availability and reactivity.

As the alkyl groups, exemplified are methyl group, ethyl group, n-propyl group, isopropyl group, n-butyl group, isobutyl group, t-butyl group, n-amyl group, neopentyl group, n-hexyl group, cyclohexyl group, n-octyl group, n-nonyl group, 2,3,4-trimethyl-3-pentyl group, 2,4-dimethyl-3-pentyl group etc.; and as the aralkyl groups, exemplified are benzyl group, 2-phenylethyl group, 2-naphtylethyl group, diphenyl methyl group, etc.

As the aryl groups, exemplified are phenyl group, naphtyl group, biphenyl group, furyl group, etc.; and as the arylthio groups, exemplified are thiophenyl group etc.

As the alkenyl groups, exemplified are 2-methyl-1-propenyl group, 2-butenyl group, etc.; as the aryl alkenyl groups, exemplified are trans-β-styryl group, 3-phenyl-1-propenyl group, etc.; and as the cyclic alkenyl groups, exemplified are 1-cyclohexenyl group etc.

As the alkoxy groups, exemplified are methoxy group, ethoxy group, n-propoxy group, t-butoxy group, etc.; and as the aryloxy group, exemplified are phenoxy group, naphtyloxy group, diphenyloxy group, etc.

As the alkyloxy carbonyl groups, exemplified are methoxy carbonyl group, ethoxy carbonyl group, t-butyloxy carbonyl group, etc.; as the aralkyloxy carbonyl groups, exemplified are benzyloxy carbonyl group, etc.; and as the aryloxy carbonyl groups, exemplified are phenyloxy carbonyl group etc.

Among the above $R^1$–$R^{22}$, groups other than hydrogen atom, halogen atom, cyano group, and nitro group, may be substituted with: a halogen atom such as fluorine atom, chlorine atom, bromine atom, and iodine atom; alkoxy group sucu as methoxy group, ethoxy group, n-propoxy group, t-butoxy group, etc.; aryloxy group such as phenoxy group, etc.; lower alkyl group such as methyl group, ethyl group, n-propyl group, isopropyl group, n-butyl group, isobutyl group, t-butyl group, n-amyl group, neo pentyl group, n-hexyl group, etc.; lower alkylthio group such as n-propylthio groups, such as , and t-butylthio group, etc.; arylthio group such as phenylthio group, etc.; nitro group; hydroxyl group, etc.

Following compounds are illustrated as a concrete example of bis(diphenylvinyl)arene compound (1) of the present invention.

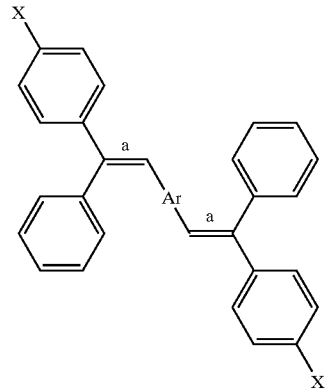

X  Br, Cl

Ar

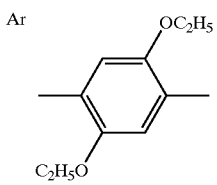 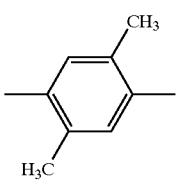 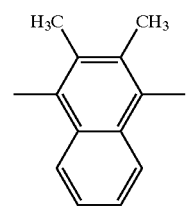

-continued

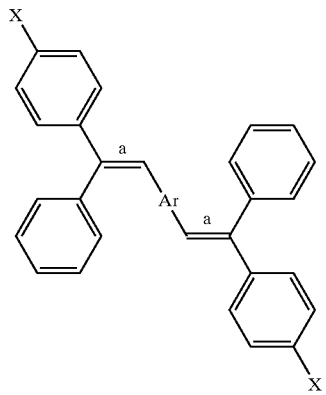

X Br, Cl

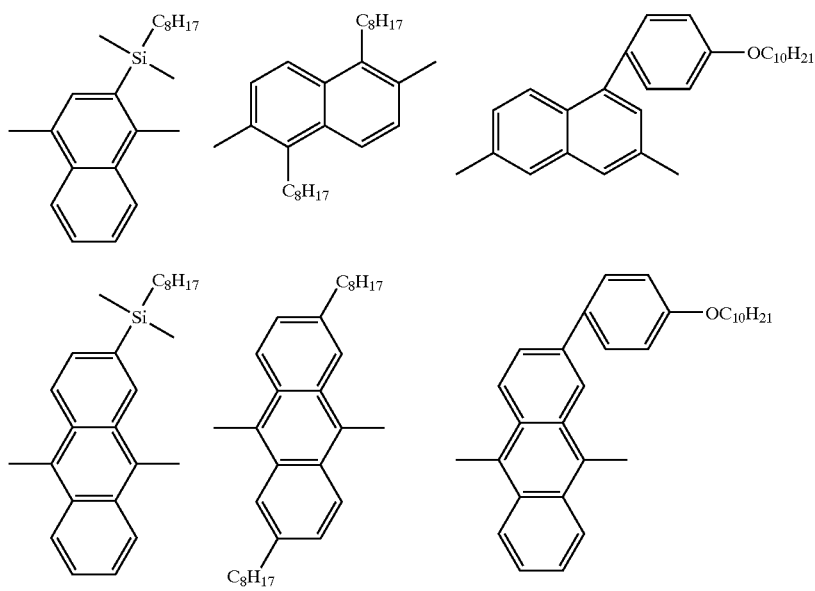

a: The olefin portion may be cis or trans.

Although the method for preparing the compound of general formula (1) of the present invention is not especially limited, compound (E) which is an example of the compound of general formula (1), can be produced, for example as shown by the following figure: by reacting a dihalomethyl aryl compound (A) with phosphorous ester (B) to produce a bis(dialkylphosphonomethyl)aryl compound (C) (step 1): and by reacting the bis(dialkylphosphonomethyl)aryl compound (C) produced in step 1 with a benzophenone compound (D) (step 2).

Step 1

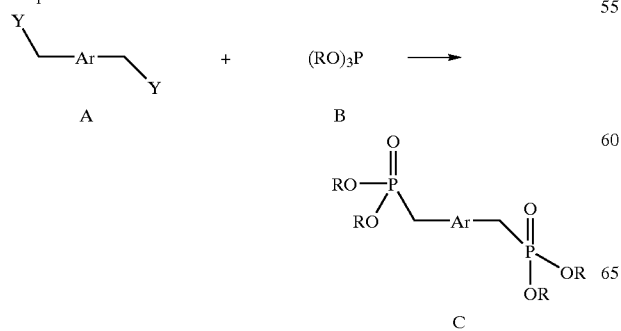

Step 2

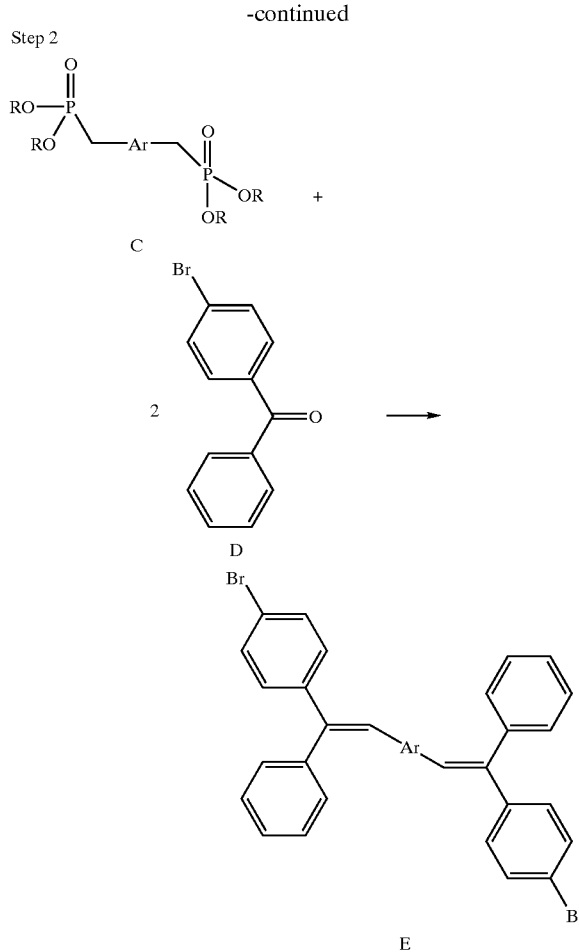

In step 1, Ar of dihalomethylaryl compound (A) is the same as exemplified about the compounds of the above formula (1). Y is a halogen atom. As halogen atoms, for example, chlorine atom, bromine atom, and iodine atom are exemplified, and bromine atom is preferable.

In step 1, as the phosphorous ester (B), trimethyl phosphite, triethyl phosphate, tri-n-propyl phosphite, etc. are exemplified, and triethyl phosphite is preferable. Step 1 is usually carried out with using phosphorous ester (B) as a solvent.

In step 1, a solvent may be mixed further. As the solvent to be mixed, for example: ether solvents such as diethyl ether, tetrahydrofuran, tertiary butylmethylether, and dioxane; hydrocarbon solvents such as hexane, cyclohexane, toluene, xylene, etc. can be used as an inert solvent under the reaction. The amount of the solvent used is not especially limited, but it is usually about 10 to 500 times to dihalomethylaryl compound (A) in a weight ratio.

When using a phosphorous ester as a solvent, the reaction temperature is usually a reflux temperature. When using other solvent with mixing, it can be made to react, if necessary at a pressurized condition, at the same temperature with the reflux temperature of the case using phosphorous ester as a solvent. Specifically, the reaction temperature is usually about from 50° C. to 250° C., and suitably from 110° C. to 180° C.

Although the reaction time is not limited especially, it is usually for about from 30 minutes to 100 hours. Usually, the time when substantially all of the raw material dihalomethylaryl compound (A) is consumed, is considered as the end of reaction, After reaction, bis(dialkylphosphonomethyl)aryl compound (C) can be obtained by distilling off the remaining phosphorous ester and solvent under reduced pressure. If necessary, from the resultant reaction concentrate, by a conventional method, for example, after mixing with a weakly basic water, such as sodium-hydrogencarbonate water etc., extraction with an organic solvent such as toluene, ethyl acetate, diethyl ether, dichloro methane, is carried out, and the desired bis(dialkylphosphonomethyl) aryl compound can be obtained by concentrating the resultant organic layer. Moreover, purification by column chromatography or distillation may be carried out according to needs.

In step 2, bis(dialkylphosphonomethyl)aryl compound (C) obtained by the above step 1 is reacted with benzophenone compound (D) under existence of abase, and compound (E) which is an example of bis(diphenyl vinyl)arene compound (1) of the present invention can be obtained.

By changing the benzophenone compound, various compounds of the present invention (1) can be produced.

The amounts of benzophenone compound (D) is usually about 0.5 to 10 mols, and preferably 1.5 to 4 mols based on 1 mol of bis(dialkylphosphonomethyl)aryl compound (C).

As the base used in step 2, exemplified are: inorganic bases such as sodium hydroxide, potassium hydroxide, etc.; alcoholate bases such as sodium methylate, potassium methylate, lithium methylate, sodium ethylate, potassium ethylate, lithium ethylate, sodium tertiary butyrate, potassium tertiary butyrate, lithium tertiary butyrate, etc.; and amide bases such as lithium amide, sodium amide potassium amide, etc. The amount of the base is not limited especially, it is usually about 1.5 to 10 mols, and suitably 2.5 to 4 mols based on 1 mol of the raw material of bis (dialkylphosphonomethyl)aryl compounds.

The reaction of step 2 is usually carried out in a solvent. As the solvent, an inert solvent is used, and exemplified are: halogenated solvents such as chloroform, dichloromethane, 1,2-dichloroethane, etc.; ether solvents such as ethyl ether, diethoxy methane, tetrahydrofuran, dimethoxy ethane, dioxane, etc.; and hydrocarbon solvents such as hexane, toluene, etc. Ether solvents are used preferably The amount of the solvent used is not limited especially, but it is usually about 0.1 to 500 times to benzophenone compound (D) in a weight ratio.

The reaction temperature is not limited especially, but it is usually about 0 to 100° C. The reaction time is about 30 minutes to 24 hours. Disappearance of the raw material bis(dialkylphosphonomethyl)aryl compound is considered as the reaction end.

If necessary, from the resultant reaction mixture, by a conventional method, for example, after mixing with dilute sulfuric acid, extraction with an organic solvent such as toluene, ethyl acetate, diethyl ether, dichloro methane, is carried out, and the desired bis(diarylvinyl)aryl compound can be obtained by concentrating the resultant organic layer. Moreover, purification by column chromatography or distillation may be carried out according to needs.

EXAMPLES

Hereafter, although the examples explain the present invention in detail, the present invention should not be construed to be limited thereto.

Example 1

Synthesis of 1,4-bis[2-(4-bromophenyl)-2-phenylethenyl]-2-(2-ethylhexyloxy)-5-methoxybenzene Under an inert atmosphere, 4-bromobenzophenone (0.783 g, 3mmol), and 1,4-bis-(diethylphosphonomethyl)-2-(2- ethylhexyloxy)-5-methoxy benzene (0.660 g, 1.23 mmol) were dissolved in tetrahydrofuran (10 g). At room temperature, tetrahydrofuran (3.28 g) solution of tert-butoxy potassium (0.414 g, 3.69 mmol) was added dropwise for 5 minutes, and successively stirred for 3.5 hours. The reaction mixture was charged into water (100 ml) and neutralized with 5% sulfuric acid. After neutralization, ethyl acetate (250 ml) was added and the organic layer was partitioned. The organic layer was washed with water and dried over anhydrous sodium sulfate. The solvent was distilled off under reduced pressure, and the resultant raw product was purified by silica gel chromatography to give the desired product. (Yield: 0.86 g, 93%)

MS Spectrum: $M^+$ 751.2, $M^+$-$C_8H_{16}$ 639.1. $^1$H-NMR(200 MHz/CDCl$_3$) ä 0.78–1.05 ppm (m, 6H), 1.15–1.70 ppm (m, 9H) 3.02–3.38 ppm (m, 5H), 6.13–6.30 ppm (m, 2H), 6.98–7.55 ppm (m, 20H).

Example 2

Synthesis of 9,10-bis[2-(4-bromophenyl)-2-phenylethenyl]anthracene

Under an inert atmosphere, 4-bromobenzophenone (3.917 g, 15 mmol), and 9,10-bis-(diethylphosphonomethyl) anthracene (2.942 g, 6.15 mmol) were dissolved in tetrahydrofuran (40 g). At room temperature, tetrahydrofuran (16.38 g) solution of tert-butoxy potassium (2.070 g, 18.45 mmol) was added dropwise for 5 minutes, and successively stirred for 3.5 hours. The reaction mixture was charged into water (100 ml) and neutralized with 5% sulfuric acid. After neutralization, the crystal was filtrated and the dissolved in tetrahydrofuran (300 ml). Then, the solvent was partly distilled off under reduced pressure, and cooled to deposit crystal. The crystal was filtrated and dried to give the desired product. (Yield: 1.10 g, 26%)

MS Spectrum: $M^+$ 693.1

Example 3

Synthesis of 1,4-bis[2-(4-bromophenyl)-2-phenylethenyl]-2-(3,7-dimethyloctyl)-5-methylbenzene Under an inert atmosphere, 4-bromobenzophenone (2.611 g, 10 mmol), and 1,4-bis(diethylphosphonomethyl)-2-(3,7-dimethyloctyl)-5-methyl benzene (2.184 g, 4.10 mmol) were dissolved in tetrahydrofuran (30 g). At room temperature, tetrahydrofuran (10.92 g) solution of tert-butoxy potassium (1.380 g, 12.30 mmol) was added dropwise for 5 minutes, and successively stirred for 3.5 hours. The reaction mixture was charged into water (200 ml) and neutralized with 5% sulfuric acid. After neutralization, ethyl acetate (250 ml) was added and the organic layer was partitioned. The organic layer was washed with water and dried over anhydrous sodium sulfate. The solvent was distilled off under reduced pressure, and the resultant raw product was purified by silica gel chromatography to give the desired product. (Yield: 1.34 g, 44%)

MS Spectrum: $M^+$ 747.2 and $M^+$-$C_9H_{18}$ 621.1. $^1$H-NMR (200 MHz/CDCl$_3$) ä 0.55–0.93 ppm (m, 9H), 0.93–1.60 ppm (m, 8H), 1.85–2.15 ppm (m, 2H), 2.15–2.53 ppm (m, 5H), 6.41–6.65 (m, 2H), 6.80–7.58 ppm (m, 20H).

Example 4

Synthesis of 1,4-bis[2-(4-bromophenyl)-2-phenylethenyl]-2-[4-(3,7-dimethyloctyloxy)phenyl] benzene Under an inert atmosphere, 4-bromobenzophenone (1.306 g, 5 mmol), and 1,4-bis(diethylphosphonomethyl)-2-[4-(3,7-dimethyloctyloxy)phenyl]benzene (2.184 g, 2.05 mmol) were dissolved in tetrahydrofuran (15 g). At room temperature, tetrahydrofuran (5.46 g) solution of tert-butoxy potassium (0.690 g, 6.15 mmol) was added dropwise for 5 minutes, and successively stirred for 3.5 hours. The reaction mixture was charged into water (100 ml) and neutralized with 5% sulfuric acid. After neutralization, ethyl acetate (150 ml) was added and the organic layer was partitioned. The organic layer was washed with water and dried over anhydrous sodium sulfate. The solvent was distilled off under reduced pressure, and the resultant raw product was purified by silica gel chromatography to give the desired product. (Yield: 1.22 g, 72%)

MS spectrum: $M^+$ 825.2, $M^+$-ph 747.2, $M^+$-ph-Br 669.2. $^1$H-NMR(200 MHz/CDCl$_3$) ä 0.80–1.05 ppm (m, 9H), 1.05–1.90 ppm (m, 10H), 3.85–4.05 ppm (m, 2H), 6.62–7.58 ppm (m, 27H).

Example 5

Synthesis of 1,4-bis[2-(4-bromophenyl)-2-phenylethenyl]-2-dimethyloctylsilyl benzene Under an inert atmosphere, 4-bromobenzophenone (1.306 g, 5 mmol), and 1,4-bis(diethylphosphonomethyl)-2-dimethyloctylsilyl benzene (1.125 g, 2.05 mmol) were dissolved in tetrahydrofuran (15 g). At room temperature, tetrahydrofuran (5.46 g) solution of tert-butoxy potassium (0.690 g, 6.15 mmol) was added dropwise for 5 minutes, and successively stirred for 3.5 hours. The reaction mixture was charged into water (100 ml) and neutralized with 5% sulfuric acid. After neutralization, ethyl acetate (200 ml) was added and the organic layer was partitioned. The organic layer was washed with water and dried over anhydrous sodium sulfate. The solvent was distilled off under reduced pressure, and the resultant raw product was purified by silica gel chromatography to give the desired product. (Yield: 1.29 g, 83%)

MS spectrum: $M^+$ 763.2. $^1$H-NMR(200 MHz/CDCl$_3$) ä 0.05–0.35 ppm (m, 6H), 0.60–0.82 (m, 2H), 0.82–1.05 (m, 3H), 1.17–1.45 (m, 12H), 6.55–6.78 (m, 2H), 6.78–7.55 (m, 21H).

Referential Example 1

Synthesis of 1,4-bis[2-(4-chlorophenyl)-2-phenylethenyl]-2-(2-ethylhexyloxy)-5-methoxybenzene Under an inert atmosphere, 4-chlorobenzophenone (0.650 g, 3 mmol), and 1,4-bis(diethylphosphonomethyl)-2-(2-ethylhexylxoy)-5-methoxy benzene (0.660 g, 1.23 mmol) are dissolved in tetrahydrofuran (10 g). At room temperature, tetrahydrofuran (3.28 g) solution of tert-butoxy potassium (0.414 g, 3.69 mmol) is added dropwise for 5 minutes, and successively stirred for 3.5 hours. The reaction mixture is charged into water (200 ml) and neutralized with5% sulfuric acid. After neutralization, a hydrophobic solvent is added and the organic layer is partitioned. The organic layer is washed with water and dried over anhydrous sodium sulfate. The solvent is distilled off under reduced pressure, and the resultant raw product is purified by silica gel chromatography or recrystallization to give a desired product.

Referential Example 2

Synthesis of 9,10-bis[2-(3-bromophenyl)-2-phenylethenyl]anthracene

Under an inert atmosphere, 3-bromobenzophenone (3.917 g, 15 mmol), and 9,10-bis(diethylphosphonomethyl)

anthracene (2.942 g, 6.17 mmol) are dissolved in tetrahydrofuran (40 g). At room temperature, tetrahydrofuran (16.38 g) solution of tert-butoxy potassium (2.070 g, 18.45 mmol) is added dropwise for 5 minutes, and successively stirred for 3.5 hours. The reaction mixture is charged into water (200 ml) and neutralized with 5% sulfuric acid. After neutralization, a hydrophobic solvent is added and the organic layer is partitioned. The organic layer is washed with water and dried over anhydrous sodium sulfate. The solvent is distilled off under reduced pressure, and the resultant raw product is purified by silica gel chromatography or recrystallization to give a desired product.

Referential Example 3

Synthesis of 1,4-bis[2-(4-bromophenyl)-2-phenylethenyl]-2,5-diethoxybenzene

Under an inert atmosphere, 4-bromobenzophenone (2.611 g, 10 mmol), and 1,4-bis(diethylphosphonomethyl)-2,5-diethoxybenzene (1.912 g, 4.10 mmol) are dissolved in tetrahydrofuran (30 g). At room temperature, tetrahydrofuran (10.92 g) solution of tert-butoxy potassium (1.380 g, 12.30 mmol) is added dropwise for 5 minutes, and successively stirred for 3.5 hours. The reaction mixture is charged into water (200 ml) and neutralized with 5% sulfuric acid. After neutralization, a hydrophobic solvent is added and the organic layer is partitioned. The organic layer is washed with water and dried over anhydrous sodium sulfate. The solvent is distilled off under reduced pressure, and the resultant raw product is purified by silica gel chromatography or recrystallization to give a desired product.

Referential Example 4

Synthesis of 1,4-bis[2-(4-bromophenyl)-2-phenylethenyl]-2,5-dimethylbenzene

The above compound is obtained with the same manner as Referential Example 3, except that 1,4-bis(diethylphosphonomethyl)-2,5-diethylbenzene (1.666 g, 4.10 mmol) is used in place of 1,4-bis(diethylphosphonomethyl)-2,5-diethoxybenzene(1.912 g, 4.10 mmol).

Referential Example 5

Synthesis of 1,4-bis[2-(4-bromophenyl)-2-phenylethenyl]-2,3-dimethylnaphthalene

The above compound is obtained with the same manner as Referential Example 3, except that 1,4-bis(diethylphosphonomethyl)-2,3-dimethylnaphthalene (1.871 g, 4.10 mmol) is used in place of 1,4-bis(diethylphosphonomethyl)-2,5-diethoxybenzene(1.912 g, 4.10 mmol).

The bis(diphenylvinyl)arene compound having a reactive functional group on phenyl group of the present invention has sufficient solubility in an organic solvent and excellent reactivity, and can be preferably used as a raw material for a polymer of a light-emitting material.

What is claimed is:

1. A bis(diphenylvinyl)arene compound represented by general formula (1):

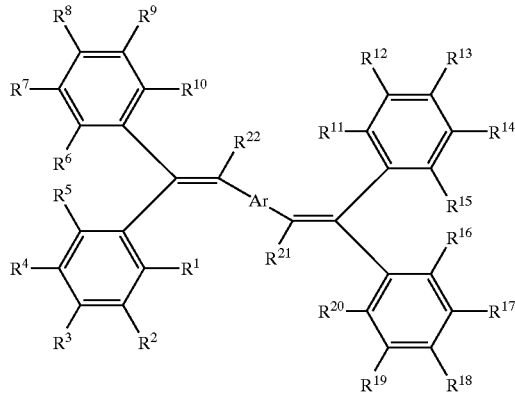

wherein, Ar is an arylene group selected from a group consisting of a phenylene group, a naphthalenediyl group and an anthracenediyl group, and has one or more substituents selected from alkylsilyl group, alkoxy phenyl group, arylsulfonyloxy group, alkylsulfonyloxy group, alkyl group, alkenyl group, aralkyl group, arylthio group, aryl alkenyl group, cyclic alkenyl group, alkoxy group, aryloxy group, alkyloxy carbonyl group, aralkyloxy carbonyl group, aryloxy carbonyl group, and aryl group; $R^1$–$R^{22}$ each independently represent a hydrogen atom, a halogen atom, cyano group, nitro group, arylsulfonyloxy group, alkylsulfonyloxy group, alkyl group, alkenyl group, aralkyl group, arylthio group, arylalkenyl group, cyclic alkenyl group, alkoxy group, aryloxy group, alkyloxy carbonyl group, aralkyloxy carbonyl group, aryloxy carbonyl group, or aryl group; and at least one of $R^1$–$R^{20}$ is a halogen atom, arylsulfonyloxy group or alkyl sulfonyloxy group.

2. The bis(diphenylvinyl)arene compound according to claim 1, wherein Ar has one or more substituents selected from alkyl group, alkylsilyl group and alkoxyphenyl group.

3. The bis(diphenylvinyl)arene compound according to claim 1 or 2, wherein $R^3$ is a halogen atom, arylsulfonyloxy group or alkylsulfonyloxy group.

4. The bis(diphenylvinyl)arene compound according to claim 1 or 2, wherein $R^3$ and $R^{13}$ are halogen atoms, arylsulfonyloxy groups or alkylsulfonyloxy groups.

5. The bis(diphenylvinyl)arene compound according to claim 3, wherein $R^3$ is a halogen atom.

* * * * *